United States Patent
Munderloh et al.

(10) Patent No.: US 12,080,384 B2
(45) Date of Patent: Sep. 3, 2024

(54) METHOD FOR COMPRESSING GENOMIC DATA

(71) Applicant: Gottfried Wilhelm Leibniz Universitaet Hannover, Hannover (DE)

(72) Inventors: Marco Munderloh, Langenhagen (DE); Jan Voges, Hannover (DE); Joern Ostermann, Hannover (DE)

(73) Assignee: GOTTFRIED WILHELM LEIBNIZ UNIVERSITAET HANNOVER, Hannover (DE)

( * ) Notice: Subject to any disclaimer, the term of this patent is extended or adjusted under 35 U.S.C. 154(b) by 1134 days.

(21) Appl. No.: 15/736,166

(22) PCT Filed: Jun. 16, 2016

(86) PCT No.: PCT/EP2016/063875
§ 371 (c)(1),
(2) Date: Dec. 13, 2017

(87) PCT Pub. No.: WO2016/202918
PCT Pub. Date: Dec. 22, 2016

(65) Prior Publication Data
US 2018/0181706 A1 Jun. 28, 2018

Related U.S. Application Data

(60) Provisional application No. 62/180,146, filed on Jun. 16, 2015.

(51) Int. Cl.
*G16B 50/50* (2019.01)
*G06F 16/174* (2019.01)
(Continued)

(52) U.S. Cl.
CPC ......... *G16B 50/50* (2019.02); *G06F 16/1744* (2019.01); *G16B 30/00* (2019.02);
(Continued)

(58) Field of Classification Search
CPC ..... G06F 16/1744; G16B 30/10; G16B 30/00; H03M 7/3059
(Continued)

(56) References Cited

U.S. PATENT DOCUMENTS

| 2011/0163898 A1 | 7/2011 | Hwang et al. |
| 2013/0204851 A1 | 8/2013 | Bhola |
| 2016/0342615 A1* | 11/2016 | Srikanth ............ G06F 16/1724 |

OTHER PUBLICATIONS

Szymon Grabowski, Sebastian Deorowicz, and Łukasz Roguski: ("Disk-based compression of data from genome sequencing", Bioinformatics, vol. 31, Issue 9, May 1, 2015, pp. 1389-1395) (Year: 2015).*

(Continued)

*Primary Examiner* — Larry D Riggs, II
*Assistant Examiner* — Guozhen Liu
(74) *Attorney, Agent, or Firm* — WC&F IP

(57) ABSTRACT

The present invention relates to a method for compressing genomic data, whereby the genomic data are stored in at least one data file containing at least a plurality of reads built by a genome sequencing method, whereby each read includes a mapping position, a CIGAR string and an actual sequenced nucleotide sequence as a local part of the donor genome, comprising the steps: —unwind a nucleotide sequence of a current read of one of said data files by using the mapping position and the CIGAR string of said current read, whereby said current read has at least one previous read, —compute a difference between the unwound nucleotide sequence of said current read and an unwound nucleotide sequence of at least one of said previous reads, whereby said difference contains the differences of the mapping (Continued)

Figure 1:
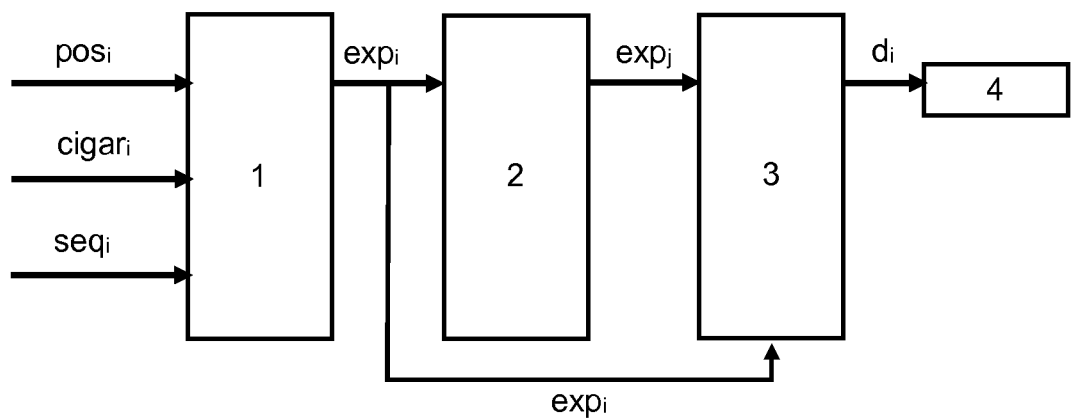

positions and the nucleotide sequences, —pass said computed difference to an entropy coder to compress said difference, —encode said current read by the compressed difference, and —repeat the forgoing steps with said current read as one of said previous reads and a following read as a new current read until no more following reads are available.

16 Claims, 2 Drawing Sheets

Specification includes a Sequence Listing.

(51) Int. Cl.
    *G16B 30/00*      (2019.01)
    *G16B 30/10*      (2019.01)
    *G16B 40/00*      (2019.01)
    *G16B 50/00*      (2019.01)
    *H03M 7/30*      (2006.01)
    *G06F 16/17*      (2019.01)

(52) U.S. Cl.
    CPC ............. *G16B 30/10* (2019.02); *G16B 40/00* (2019.02); *G16B 50/00* (2019.02); *H03M 7/3059* (2013.01)

(58) Field of Classification Search
    USPC .......................................................... 702/20
    See application file for complete search history.

(56) References Cited

OTHER PUBLICATIONS

Idoia Ochoa, Mikel Hernaez, and Tsachy Weissman: "Aligned genomic data compression via improved modeling", J Bioinform Comput Biol. Dec. 2014 ; 12(6): 1442002. (Year: 2014).*

Saha, S., Rajasekaran, S .: NRRC: A Non-referential Reads Compression Algorithm. In: Harrison, R., Li, Y., Măndoiu, I. (eds) Bioinformatics Research and Applications. ISBRA 2015. Lecture Notes in Computer Science(), vol. 9096. (Year: 2015).*

Singh, Sanjay, Anil Kumar Saini, and Ravi Saini. "Real-time FPGA based implementation of color image edge detection." International Journal of Image, Graphics and Signal Processing 4.12 (2012): 19. (Year: 2012).*

Brandon et al.; "Data structures and compression algorithms for genomic sequence data"; Bioinformatics, vol. 25, No. 14, Jul. 15, 2009, pp. 1731-1738.

White et al.; "Compressing DNA sequence databases with coil"; BMC Bioinformatics, vol. 9, No. 242, May 20, 2008, pp. 1-15.

Deorowicz et al.; "Compression of DNA sequence reads in FASTQ format"; Bioinformatics, vol. 27, No. 6, Mar. 15, 2011, pp. 860-862.

Bonfield et al.; "Compression of FASTQ and SAM Format Sequencing Data"; PLOS One, vol. 8, No. 3, Mar. 22, 2013, pp. 1-11.

Bonfield, J. K., and Mahoney, M. V., "Compression of FASTQ and SAM Format Sequencing Data," pp. 1-10, Mar. 22, 2013, Plos ONE, vol. 8, issue 3, e59190, www.plosone.org.

Numanagic, I., Bonfield, J. K., Hach, F., Voges, J., Ostermann, J., Alberti, C., Mattavelli, M., and Cenk Sahinalp, S., "Comparison of High Throughput Sequencing Data Compression Tools," pp. 1-4, Oct. 24, 2016, Nature Methods Advance Online Publication, https://doi.org/10.1038/nmeth.4037.

The SAM/BAM Format Specification Working Group, "Sequence Alignment/Map Format Specification," pp. 1-20, Oct. 18, 2018, https://samtools.github.io/hts-specs/SAMv1.pdf.

Hach, F., Numanagic, I., and Cenk Sahinalp, S., "DeeZ: Reference-Based Compression by Local Assembly," pp. 1082-1084, Nov. 2014 (available online Oct. 30, 2014), Nature Methods, vol. 11, No. 11, https://doi.org/10.1038/nmeth.3133.

Jones, D. C., Ruzzo, W. L., Peng, X., and Katze, M. G., "Compression of Next-Generation Sequencing Reads Aided by Highly Efficient de-Novo Assembly," pp. 1-9, Aug. 16, 2012, Nucleic Acids Research, vol. 40, No. 22, e171, https://doi:10.1093/nar/gks754.

Mahoney M., "Data Compression Explained," pp. 1-78, Apr. 15, 2013, http://mattmahoney.net/dc/dce.html.

Willems, F. M., Shtarkov, Y. M., and Tjalkens, T. J., "The Context-Tree Weighting Method: Basic Properties," pp. 653-664, Jan. 1, 1995, IEEE Transactions on Information Theory, vol. 41, No. 3.

Ziv, J., and Lempel, A., "A Universal Algorithm for Sequential Data Compression, " pp. 337-343, May 1977, IEEE Transactions on Information Theory, vol. 23, No. 3.

\* cited by examiner

SEQUENCE LISTING

<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: Synthetic read 1 nucleotide sequence

<400> SEQUENCE: 1
ttagataaag gatactg                                                  17

<210> SEQ ID NO 2
<211> LENGTH: 14
<212> TYPE: DNA
<213> ORGANISM: Artificial Sequence
<220> FEATURE:
<223> OTHER INFORMATION: Synthetic read 2 nucleotide sequence

<400> SEQUENCE: 2
aaaagataag gata                                                     14

<210> SEQ ID NO 3
<211> LENGTH: 18
<212> TYPE: DNA
<213> ORGANISM: Artificial Sequence
<220> FEATURE:
<223> OTHER INFORMATION: Synthetic read 1 expanded nucleotide sequence
<220> FEATURE:
<221> NAME/KEY: misc_feature
<222> LOCATION: (15)..(15)
<223> OTHER INFORMATION: n is a, c, t or g

<400> SEQUENCE: 3
ttagataaag gatanctg                                                 18

<210> SEQ ID NO 4
<211> LENGTH: 15
<212> TYPE: DNA
<213> ORGANISM: Artificial Sequence
<220> FEATURE:
<223> OTHER INFORMATION: Synthetic read 2 expanded nucleotide sequence

<400> SEQUENCE: 4
aaaagataag ggata                                                    15
```

METHOD FOR COMPRESSING GENOMIC DATA

SEQUENCE LISTING

This application includes as the Sequence Listing the complete contents of the .txt file "03101174US_sequence listing_ST25", created May 29, 2024, containing 4,096 bytes, hereby incorporated by reference.

The present invention relates to a method for compressing genomic data, whereby the genomic data are stored in at least one data file containing at least a plurality of mapped and/or aligned reads built by a genomic sequencing method, whereby each read includes a mapping position, a CIGAR string and an actual sequenced nucleotide sequence as a local part of the donor genome.

Due to novel high-throughput sequencing (HTS) and/or next-generation sequencing (NGS) technologies, the sequencing of huge amounts of genetic information has become affordable. On account of this flood of data, IT costs may become a major obstacle compared to sequencing costs. High-performance compression of genomic data is required to reduce the storage size and transmission costs.

In such data files, among other data, the nucleotide sequences, the mapping positions, the alignment information (CIGAR strings) and the quality scores are stored. This structure is, for example, described in Li et al.: "The Sequence Alignment/Map format and SAMtools", Bioinformatics, 25(16), 2078-9, (2009). As a preprocessing step, the mapping position and alignment information might be computed from the raw nucleotide sequences and quality scores produced by a genomic sequencing method.

One file format intended for the storage of such mapped and/or aligned reads is the sequence alignment/map format (SAM). Mapped and/or aligned sequencing data contains more redundancy than the raw nucleotide sequences and quality scores, as typically multiple reads are mapping to the same location on the donor genome.

In the present patent application, a read includes a mapping position, an alignment information (denoted as "CIGAR string") and an actual sequenced nucleotide sequence, whereby a plurality of reads are stored in at least one appropriate file.

In the present patent application, the mapping position relates to the start or the begin of the actual sequenced nucleotide sequence of the corresponding read in view of the donor genome or a reference genome used for alignment.

In the present patent application, a CIGAR string (alignment information) encodes the similarities and divergences between the actual sequenced nucleotide sequence of the corresponding read and the nucleotide sequence of the donor genome or the reference genome used for alignment.

In Ziv et al.: "A universal algorithm for sequential data compression" IEEE Transactions on Information Theory 23(3), 337-343, (1977), a general purpose method to compress data is known. Further, it has been shown by Tembe et al.: "G-SQZ: compact encoding of genomic sequence and quality data", Bioinformatics, 26(17), 2192-4, (2010), and Deorowicz et al.: "Compression of DNA sequence reads in FASTQ format", Bioinformatics, 27(6), 860-2, (2011), that splitting the data into separate streams for sequence reads, quality scores etc. (and compressing them independently) yields significant gains over general-purpose method.

It is an aspect of the present invention to provide a better compression method for compressing mapped and/or aligned genomic data. It is a further aspect of the present invention to provide a decompression method for decompressing such compressed genomic data.

The problem is solved by the method according to claim 1.

According to claim 1, a method for compressing genomic data is proposed. The genomic data are stored in an appropriate data file or files, for example in a SAM file, and include at least a plurality of reads built by a genomic sequencing method. Each read includes a mapping position, a CIGAR string and an actual sequenced nucleotide sequence as a local part of the donor genome.

Further, a nucleotide sequence of a current read of the mapped sequencing data file is unwound by using the mapping position and the CIGAR string of said current read. In general, unwinding the nucleotide sequence consists of a series of insertion, deletion and modification operations as described by the CIGAR string. Consequently, unwinding the sequence condenses the position, the CIGAR string and the nucleotide sequence into a joint representative code word. Said current read has at least one previous read except the current read is the first read. Normally, reads are plotted line by line in the data file and one a read is represented by a full line in the data file.

Further, a difference between the unwound nucleotide sequence of said current read and an unwound nucleotide sequence of at least one of said previous reads is computed. The nucleotide sequence of the previous read or reads could be unwound before or during the compression.

The difference between both unwound nucleotide sequences contains the differences of the mapping positions and the nucleotide sequences. The computation of a difference between nucleotide sequences is prior art and well-known.

Furthermore, the computed difference is passed to an entropy coder to compress said difference, whereby the current read is encoded (e.g. replaced) by the compressed difference for storage or transmission, e.g. as a bit stream. Such entropy coder could be a multitude of entropy coders. Furthermore, before passing the computed difference to the entropy coder, the difference is passed to a prediction module or multiple prediction modules and then the output is passed to the entropy coder.

After these, the steps are repeated with said current read as one of said previous reads and the following read, especially a consecutive following read in the next line of the data file or files, as the new current read until no more reads are available in the files.

This method is in general used for the second read to the last read in the data file. For the special case of the first read (because there is no previous read) it exists a variation of the begin and the selection of a reference read (previous read).

The proposed compression method uses a short-time memory of arbitrary size which may be implemented as a sliding window (with one or more previous reads regarding to the current read) to perform a local implicit assembly. The inventive method does not require a reference genome to compress the genomic data. The inventive method performs the compression by using (only) the currently available nucleotide sequences in the short-time memory. This short-time memory can be re-initialized at any time, enabling non-sequential (i.e. random) access to any part of the compressed data without the need of decoding the preceding compressed data.

The inventive method is based on correlations between consecutive reads. As all reads in a SAM file are aligned to their mapping position, all reads (nucleotide sequences) mapped to the same position should be similar, except for gene mutations (SNP) or sequencing errors, respectively mapping errors. These aberrations are coded in the CIGAR string. The proposed method encodes sequence reads blockwise exploiting the joint coding of mapping positions, CIGAR strings and the sequence reads themselves, whereas the block size might be fixed or variable and of arbitrary size. The first sequence read in a block can be encoded without prediction, as well as the corresponding mapping position and the CIGAR string. However, it might also be coded against some arbitrary reference read.

Preferably, said computed difference is passed to said entropy coder for lossless compression of said difference.

In a preferred embodiment, said current read has a number of consecutive previous reads so that more than one previous read is used to compute differences. Therefore, a difference between the unwound nucleotide sequence of said current read and the unwound nucleotide sequence of at least two of said consecutive previous reads is computed, whereby a difference from said computed differences is selected. The selected difference indicates a minimum difference or distinction between the unwound nucleotide sequence of said current read and the unwound nucleotide sequence of said corresponding previous read. Sequence reads, which are not aligned might be directly passed to the entropy coder or retained and encoded separately later, e.g. at the end of each block. The matching read (regarding to the selected difference) might be a signaled or estimated at the decoder. The selected difference is passed to the entropy coder to compress said difference.

The current read is encoded (e.g. replaced) by the compressed difference including an identification of the previous read, on which the computed difference between the corresponding nucleotide sequences is based. Therefore, a decoder could decode the nucleotide sequence of the current read based on the computed difference and an identification of the previous read. The identification could be a line number within the file or a position.

In a further embodiment, the number of consecutive previous reads is a fixed number greater than 2, if a fixed number of consecutive previous reads exists. In practice, the number of previous reads could be 100. If the difference is compressed and the current read is encoded, the current read is added to the fixed number of previous reads as a youngest read and the oldest read is deleted from the fixed number of previous reads. Therefore, a sliding window line by line through all reads of the data file can be implemented.

In another embodiment, the number of consecutive previous reads is variable.

In a further embodiment, for each computed difference a distance as an arbitrary metric, especially an entropy as a distance of an arbitrary metric, is computed. A distance is selected in the selection step, which has a minimum distance, e.g. a minimum entropy.

In a further embodiment, a consensus unwound nucleotide sequence is computed based on unwound nucleotide sequences of consecutive previous reads by building a consensus of each unwound nucleotide of the unwound nucleotide sequences of said consecutive previous reads. Said consensus read is used as a previous read for computing a difference between said current read and said consensus read as a previous read.

If a current read has no previous reads, a difference is computed between the unwound nucleotide sequence of said current read and an unwound nucleotide sequence of an arbitrary read (selected or computed as a consensus read) of the mapped sequencing data as a previous read.

In another embodiment, if the current read has no previous reads, the mapping position, the CIGAR string and the actual nucleotide sequence of the current read is (directly) passed to an entropy coder to compress the read and said current read is encoded (e.g. replaced) by said compressed read.

In a further embodiment, at least one of said data file, for example a SAM file, contains a plurality of reads as well as a plurality of corresponding quality scores. The quality score values of each nucleotide sequence of a read is contained in one of the files as a quality score line, whereby a plurality of quality score lines were contained in one of the files. The quality score values of a quality score line evaluate the sequencing quality of the corresponding nucleotides a corresponding read.

For compressing the quality scores, a prediction quality score value for an actual quality score value at a current position within a current quality score line is predicted. The prediction of the prediction quality score value is conducted by evaluating a plurality of consecutive previous quality score values based on the current position within the current quality score line and one or more quality score values of previous quality score lines at the same current position by a predictor or a predictor module.

Further, a difference between said prediction quality score value and the actual quality score value at the current position is computed and passed to an entropy coder. Further, the steps of predicting the prediction quality score value and computing the difference is repeated for each actual quality score value in the current quality score line, for example by using a next position in the current quality score line. If all quality score values of a current quality score line are predicted and for each value a difference is computed, the current quality score line is encoded (e.g. replaced) by an output of said entropy coder (or multiple entropy coder) including a compression of said differences of said current quality score line. Based on all differences of one current quality score line, a compression of the quality score line is computed by the entropy coder.

Furthermore, these steps are repeated with a following quality score line until no more quality score lines are available.

As an alternative to building the prediction memory during the decoding process, the possibility to store the prediction table (generated during compression) e.g. in a file header to speed up the compression as an alternative or in combination are proposed. The prediction table for the individual blocks may then be encoded separately. This enables non-sequential (i.e. random) access to the compressed data by retaining the compression performance of the prediction model (e.g. Markov model) by providing the fully trained prediction memory, or parts of it (built from the full input data at the encoder) to the decoder, which can then be directly used from the start of the decoding process.

Due to the large alphabet of the quality scores (typically approximately 30 symbols, also more are theoretical possible), mark of models are limited to some low order N (typically N<3). As an alternative, a FIR filter is used to predict the current symbol.

In a further embodiment, a linear predictor to compute said prediction quality score value is used to evaluate the linear series of previous quality score values weighted with predictor coefficients.

$$q_{N+1}^{(p)} = \Sigma_{n=1}^{N} a_n q_n$$

One possible approach to compute the predictor coefficients is to minimize the mean squared error, which yields the following condition to compute the filter coefficients.

$$\frac{\partial}{\partial a_n}(E[(q_{n+1} - q_{N+1}^{(p)})^2]) = 0$$

Therefore, a set of predictor coefficients for a quality score line is obtained. Sets of predictor coefficients might be shared among multiple quality score lines.

As an alternative to said minimum mean square error filtering, it is possible to employ any other known methods to compute the predictor coefficients, e.g. with minimum variance prediction.

In a further embodiment, said current quality score line has a number of previous quality score lines, whereby an identification vector for each previous quality score line (or a part of it) of said number of previous quality score lines is computed and once the specific quality score line is selected from said number of previous quality score lines based on an identification vector distance, for example this quality score line with a least identification vector distance. Said selected specific quality score line is used in the prediction step as a previous quality score line.

It has been observed that in some data sets subsequent quality score lines are similar in terms of a small Levensthein distance between pairs of quality score lines. To respond this, a so-called line context is used, a structure holding some number of previous lines from the quality score lines of at least one of the files. The prediction context is divided into one part containing the memory locations on the current line (intra-line memory) and one part containing the memory locations on some specific line or lines from the line context (inter-line memory). An identification vector for each quality score line (or parts of it) in the line context is concluded. As an example, this could be a three-dimensional vector, containing e.g. the length, the mean, and the variance of a quality score line. At the process of encoding the current quality score line, one specific quality score line from the line context is selected with the least identification vector distance whereas any known vector distance measurement made be applied, e.g. with three-dimensional or Euclidean distance. The vector components might be individual weighted.

Furthermore, it is an aspect of the present invention to decompress genomic data, which were compressed by one of the methods mentioned above. Each current read is reconstructed from at least one of the previous reads by applying the decompressed difference of said current read to reconstruct the nucleotide sequence, the CIGAR string and the mapping position of said current read. If a compression (encoding) algorithm is known, the decompression (decoding) algorithm is also known and can be directly derived from the compression algorithm.

In accordance to this, compressed quality scores can be decompressed.

Figure 2:
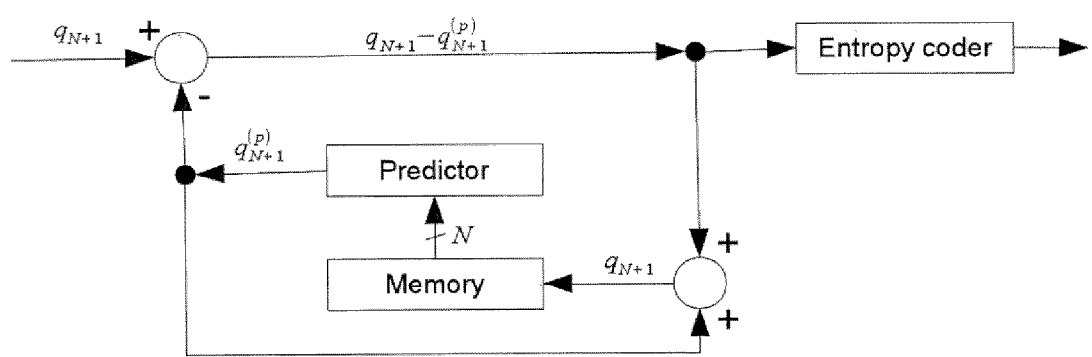

The present invention is described in more detail by reference to the following figures:

FIG. 1—possible encoder structure of the proposed sequence for compression algorithm;

FIG. 2—layout of a predictive encoder.

FIG. 1 shows a possible encoder structure of the proposed sequence compression algorithm. The current read i>1 should be compressed. The read$_i$ has a CIGAR$_i$-string, pos$_i$ and seq$_i$ as nucleotide sequence. These three data parameters of the read$_i$ are passed to an expand module 1.

The expand module unwinds the nucleotide sequence seq$_i$ of the current read$_i$ by using the mapping position pos$_i$ and the CIGAR string CIGAR$_i$. The result of the expand module is a joint sequence exp$_i$.

The exp$_i$ code word is passed to a ring buffer 2. The ring buffer 2 is a last in last out container, especially of adaptable and variable size, so that the N previously expanded reads are memorized. Each expanded read exp$_j$, 1≤j<i is compared with the current unwound nucleotide sequence exp$_i$ to compute a difference between the unwound nucleotide sequence exp$_i$ of the current read and the unwound nucleotide sequence exp$_j$ of the previous reads using a difference module 3. The computed difference with the least difference between compared nucleotide sequences is used for compressing the corresponding read. D$_i$ is passed to an entropy coder 4 to compress the current read i as a difference to the best fitted previous read.

A possible implementation of the algorithm in pseudo-code is shown in the following, where "read 1"=SEQ ID NO: 1, "Read 2"=SEQ ID NO: 2, "read 1 expanded"=SEQ ID NO: 3 and "read 2 expanded"=SEQ ID NO: 4.

```
Input: block_size, threshold, pos[L], cigar[L], seq[L], L (no. of SAM records)
Output: binary stream (from entropy coder)
new circbuf(N); // circular buffer of size N (sliding window)
l = 0;           // line count
b = block_size; // block line count
while (l < L)
|  if (b == block_size) then // start new block
|  |  clear_circbuf( );
|  |  reset_entropy_coder( );
|  |  entropy_coder(pos[l], cigar[l], seq[l]);
|  |  circbuf.push(pos[l], cigar[l], seq[l]);
|  |  b = 1;
|  else
|  |  if (cigar(l) != '*') then // sequence is mapped
|  |  |  min_entropy = +inf;
|  |  |  do
|  |  |  |  seq_exp = expand(pos[l], cigar[l], seq[l]);
|  |  |  |  (pos_ref, cigar_ref, seq_ref, ref_index) =
|  |  |  |      circbuf.get_next( );
|  |  |  |  ref_exp = expand(pos_ref, cigar_ref, seq_ref);
|  |  |  |  d = compute_differences(seq_exp, ref_exp);
|  |  |  |  if (entropy(d) < min_entropy) then
|  |  |  |  |  min_entropy = entropy(d);
|  |  |  |  |  ref_index_best = ref_index;
|  |  |  |  |  d_best = d;
|  |  |  |  endif
|  |  |  while (entropy(d) > threshold) && circbuf.has_next( );
|  |  |  entropy_coder(ref_index_best, d_best);
|  |  else
|  |  |  entropy_coder(pos[l], cigar[l], seq[l]);
|  |  endif
|  |  circbuf.push(pos(l), cigar(l), seq(l));
endif
|  b++;
|  l++;
endwhile
```

The short working principle of the function "expand" is given by the following.

```
POS  CIGAR       SEQ
7    8M2I441D3M  TTAGATAAAGGATACTG   < read 1

9    3S6M1P1I4M  AAAAGATAAGGATA      < read 2
```

```
6789... < POS
8M      2I4M 1D3M
TTAGATAAAGGATA_CTG       < read 1 expanded

AAAAGATAAGGGATA          < read 2 expanded 3S 6M 1P1I4M
```

A basic layout of a predictive encoder to compress the quality score lines is shown in FIG. 2. The memory used by the predictor is derived from the quality score line values $q_n$ in the line before the current position and from quality score line values from other quality score lines at the same position. Thus, it could be beneficial to share previously computed predictor coefficients among multiple lines.

The basic idea is that the previous quality score values in the same quality score line and a quality score value of a previous quality score line is used to predict a current quality score value.

```
Line î  DECEEEECDDDDDDDDDDDDDDEDCDDD

Line i  DDDDDDDCDDDDDBDDDDDDDDEEEDDD
```

Line i is the current quality score line. The bold/italic D is the prediction quality score value at a current position that is to be predicted. Line î is the specific quality score line and the bold D is one of a quality score value for the predictor. The 2 bold D in the current line i are the other quality score values for the predictor to predict the bold/italic D of the prediction quality score value.

---

The invention claimed is:

1. A computer implemented method for reducing computer storage size requirements for and transmission costs for transmitting genomic data, via a compressing of genomic data stored in at least one data file as a plurality of reads built by a genome sequencing method, each read including a read mapping position, a read Compact Idiosyncratic Gapped Alignment Report (CIGAR) string, comprising a compressed pairwise alignment format report defining a sequence of matches/mismatches and deletions or gaps, and a read actual sequenced nucleotide sequence that is a local part of a donor genome, the computer implemented method comprising:
   a sequence of computer processing steps, including:
   a computer processing step of initializing a window buffer memory,
   a computer processing step of selecting one of the reads as a current read,
   a computer processing step of expanding the current read to an unwound nucleotide sequence of the current read, using the mapping position and the CIGAR string of said current read,
   a computer processing step, conditional on no current storage in the window buffer memory of any previous read-based unwound nucleotide sequences, comprising computing an initial read difference, passing said initial read difference to a computer-implemented entropy encoder,
   a computer processing step, by the computer implemented entropy encoder, upon receiving said computed initial read difference, of compressing said computer initial read difference to a compressed initial read difference, and replacing encoding said current read by the compressed initial difference, wherein the initial read difference is based on the unwound nucleotide sequence of the current read and another data,
   a computer processing step, conditional on a current storage in the window buffer memory of at least one previous read-based unwound nucleotide sequences, each corresponding to a respective expanding of a different previous read, comprising:
      computing a computed difference between the unwound nucleotide sequence of said current read and each of said at least one previous read-based unwound nucleotide sequences,
      selecting, as a selected difference, a one from said at least one computer differences that indicates a minimum,
      passing said computed difference to a computer-implemented entropy encoder, and including in said computed difference, the difference of the current read mapping position and at least one previous read mapping positions and the difference of the current read unwound nucleotide sequence and at least one previous read unwound nucleotide sequences, and
   a computer processing step, by the computer implemented entropy encoder, upon receiving said computed difference, of entropy encoding compressing said computed difference to a compressed difference, and replacing said current read by the compressed difference, and
   repeating said sequence of computer steps, using for each repeat of the sequence the current read as one of said previous reads and a following read as a new current read, until no more following reads are available,
   wherein, in the repeating said sequence of computer processing steps, upon said current read having a predetermined number of consecutive previous reads, the predetermined number being at least two:
      the step of computing the computed difference includes computing at least two computed differences, each a respective computed difference between the unwound nucleotide sequence of said current read and an unwound nucleotide sequence of a corresponding one among each of at least two of said consecutive reads and selecting, as a selected difference, a one from said at least two computer differences that indicates a minimum, and
      the computer processing step of passing said computed difference to said entropy encoder is configured to pass said selected difference.

2. A computer implemented method according to claim 1, wherein the computer processing step of compressing the computed difference to a compressed difference includes lossless compression of said difference.

3. A computer implemented method according to claim 1, wherein, in the sequence of computer processing steps, upon the number of consecutive previous reads being greater than a predetermined number greater than one, the sequence of computer processing steps further includes a processing step of adding said current read to the number of previous reads as a youngest read and deleting the oldest read from the number of previous reads.

4. A computer implemented method according to claim 1, wherein the computer processing step of selecting the selected difference includes:
   computing a distance for each computed difference, using entropy as a distance metric, and
   selecting, as the selected difference, the one from said at least two computed differences that indicates a minimum distance.

5. Method according to claim 1, whereby a consensus unwound nucleotide sequence is computed based on unwound nucleotide sequences of consecutive previous reads by building a consensus of each unwound nucleotide of the unwound nucleotide sequences of consecutive previous reads and whereby said consensus read is used as a previous read for computing said difference.

6. Method according to claim 1, whereby for a current read, which has no previous reads, a difference is computed between the unwound nucleotide sequence of said current read and an unwound nucleotide of an arbitrary read of the mapped sequencing data as a previous read.

7. Method according to claim 1, whereby for a current read, which has no previous reads, the mapping position, the CIGAR string and the actual nucleotide sequence of the current read is directly passed to an entropy encoder to compress the read and said current read is replaced by said compressed read.

8. Method according to claim 1 wherein at least one of said data files contains a plurality of quality score lines, whereby each quality score line includes a plurality of quality score values which evaluate the sequencing quality of a corresponding nucleotide of a nucleotide sequence of a read, comprising the steps for compressing the quality scores:
   predict a prediction quality score value for an actual quality score value at a current position within a current quality score line by evaluating a plurality of consecutive previous quality score values of said current quality current quality score lines at the same current position by a predictor, compute a difference between said prediction quality score value and the actual quality score value at the current position and pass the computed difference to an entropy encoder, repeat the predicting and computing steps for each actual quality score value of the current quality score line, replace said current quality score line by an output of said entropy encoder including all compressed differences of said current quality score line, and repeat all of the forgoing steps with a following quality score line until no more quality score lines are available.

9. Method according to claim 6, whereby said predictor is a linear predictor to compute said prediction quality score value by evaluating a linear series of previous quality score values weighted with predictor coefficients.

10. Method according to claim 6, whereby said current quality score line has a number of previous quality score lines, whereby an identification vector for each previous quality score line or a part of it of said number of previous quality score lines is computed and one specific quality score line is selected from said number of previous quality score lines with a least identification vector distance, whereby said selected specific quality score line is used in the prediction step as a previous quality score line.

11. Method according to claim 8, whereby said identification vector could be a three-dimensional vector containing a length of the quality score line, an arithmetic mean and/or a variance of a quality score line.

12. A computer readable medium storing computer executable instructions that, when performed by a computer, cause the computer to execute a compression processing steps of the method according to claim 1.

13. A hardware processing device arranged to perform the computer processing steps of the compression method according to claim 1.

14. A computer implemented method according to claim 1, further comprising computer steps including:

generating a compressed genomic data by performing a computer implemented compressing method in accordance with claim 1;

storing the compressed genomic data, in a memory resource, as a stored compressed genomic data;

performing a computer implemented decompressing the stored compressed genomic data, by computer processing steps including:

reconstructing each current read from at least one of the previous reads by steps of applying the decompressed difference of said current read to reconstruct the nucleotide sequence, the CIGAR String and the mapping position of said current read.

15. A computer readable medium storing computer executable instructions that, when performed by a computer, cause the computer to execute the computer processing steps of the decompression method according to claim 14.

16. A hardware processing device arranged to perform the computer processing steps of the decompression method according to claim 14.

* * * * *